US009603828B2

(12) United States Patent
Damireddi et al.

(10) Patent No.: US 9,603,828 B2
(45) Date of Patent: Mar. 28, 2017

(54) SULFORAPHANE ISOLATION AND PURIFICATION

(71) Applicant: PharmAgra Labs, Inc., Brevard, NC (US)

(72) Inventors: Sahadeva Reddy Damireddi, Brevard, NC (US); Kpakpo Ambroise Akue, Asheville, NC (US); Jared K. Nelson, Pisgah Forest, NC (US); Albert Roger Frisbee, Hendersonville, NC (US); Peter Wyatt Newsome, Horseshoe, NC (US)

(73) Assignee: PharmAgra Labs, Inc., Brevard, NC (US)

( * ) Notice: Subject to any disclaimer, the term of this patent is extended or adjusted under 35 U.S.C. 154(b) by 0 days.

(21) Appl. No.: 14/404,781

(22) PCT Filed: May 31, 2013

(86) PCT No.: PCT/GB2013/051457
§ 371 (c)(1),
(2) Date: Dec. 1, 2014

(87) PCT Pub. No.: WO2013/179056
PCT Pub. Date: Dec. 5, 2013

(65) Prior Publication Data
US 2015/0119359 A1    Apr. 30, 2015

Related U.S. Application Data

(60) Provisional application No. 61/654,300, filed on Jun. 1, 2012.

(51) Int. Cl.
| | |
|---|---|
| *A61K 31/275* | (2006.01) |
| *A61K 47/48* | (2006.01) |
| *C08L 5/16* | (2006.01) |
| *C07C 331/20* | (2006.01) |
| *C08B 37/16* | (2006.01) |
| *B82Y 5/00* | (2011.01) |

(52) U.S. Cl.
CPC ........ *A61K 31/275* (2013.01); *A61K 47/4823* (2013.01); *A61K 47/48969* (2013.01); *B82Y 5/00* (2013.01); *C07C 331/20* (2013.01); *C08B 37/0015* (2013.01); *C08L 5/16* (2013.01)

(58) Field of Classification Search
None
See application file for complete search history.

(56) References Cited

U.S. PATENT DOCUMENTS 5,411,968 A    5/1995    Tyers
7,879,822 B2    2/2011    Dagan et al.

FOREIGN PATENT DOCUMENTS

| CN | 102423492 A | 4/2012 |
|---|---|---|
| CN | 102688219 A | 9/2012 |
| WO | 2008091608 A1 | 7/2008 |

OTHER PUBLICATIONS

Recrystallization technique, Internet Article, http://erowid.org/archive/rhodium/chemistry/equipment/recrystallization.html, May 2006.*
International Search Report for Application No. PCT/GB2013/051457 dated Aug. 19, 2013.
Schmid H. and Karrer, P.; Helvetica Chimica Acta. 1948; 31; 6: 1497-1505.
wu H et al: "Preparation and stability investigation of the inclusion complex of sulforaphane with hydroxypropyl-beta-cyclodextrin", Carbohydrate Polymers, Applied Science Publishers, Ltd. Barking, GB, vol. 82, No. 3, Oct. 15, 2010, pp. 613-617, XP027206323.

* cited by examiner

*Primary Examiner* — Layla Berry
(74) *Attorney, Agent, or Firm* — Burns & Levinson LLP; Shawn P. Foley

(57) ABSTRACT

The present invention relates to methods of isolating and purifying sulforaphane. More specifically, the present invention relates to methods of isolating and purifying sulforaphane from natural sources. The present invention also relates to methods of forming high purity complexes of sulforaphane with cyclodextrin.

12 Claims, No Drawings

US 9,603,828 B2

SULFORAPHANE ISOLATION AND PURIFICATION

CROSS-REFERENCE TO PRIORITY APPLICATIONS

The present application is a national phase entry under 35 U.S.C. §371 of International Application No. PCT/GB2013/051457 filed May 31, 2013, published in English, which claims priority from U.S. Provisional Patent Application No. 61/654,300 filed Jun. 1, 2012, all of which are incorporated herein by reference.

FIELD OF THE INVENTION

The present invention relates to methods of isolating and purifying sulforaphane, or analogs thereof. More specifically, the present invention relates to methods of isolating and purifying sulforaphane, or analogs thereof, from natural sources. The present invention also relates to methods of forming high purity complexes of sulforaphane, or analogs thereof, with cyclodextrin.

BACKGROUND OF THE INVENTION

Sulforaphane is known to possess antimicrobial activity and the ability to inhibit carcinogenesis and tumorigenesis. It is therefore a potentially useful agent for the treatment and prevention of microbial infections and/or cancer.

Sulforaphane is found in the cruciferous vegetables such as cabbage, broccoli, broccoli sprouts, brussel sprouts, cauliflower, cauliflower sprouts, bok choy, kale, collards, arugula, kohlrabi, mustard, turnip, red raddish, and water cress. In the plant, it is present in bound form as glucoraphanin, a glucosinolate. In nature, sulforaphane is often formed from glucoraphanin following plant cell damage by an enzymatic reaction.

Various synthetic methods of producing sulforaphane are known in the art. Sulforaphane was synthesized as early as 1948 by Schmid and Karrer (Schmid H. And Karrer, P.; *Helvetica Chimica Acta.* 1948; 31; 6: 1497-1505). The Schmid synthesis results in a racemic mixture. Other methods of synthesising sulforaphane developed since 1948 also result in a racemic mixture.

One major problem associated with sulforaphane is its physical instability. Sulforaphane exists in the form of an unstable oil which rapidly degrades under normal conditions. This makes sulforaphane exceptionally hard to manufacture and distribute.

One approach to stabilise sulforaphane involves the formation of sulforaphane-cyclodextrin complexes. In this regard, U.S. Pat. No. 7,879,822B2, the entire contents of which are hereby incorporated by reference, describes a synthetic process for preparing sulforaphane followed by its subsequent stabilisation by the formation of a sulforaphane-cyclodextrin complex.

However, there still remains a need for processes that enable the efficient and effective isolation and purification of sulforaphane from its various natural sources.

SUMMARY OF THE INVENTION

In one aspect, the present invention relates to a method of isolating sulforaphane and/or a sulforaphane analog from a natural source thereof, the method comprising:

a) mixing the natural source of sulforaphane and/or sulforaphane analog with cyclodextrin in a suitable solvent, and with or without heat;
b) cooling or controlling the temperature of the mixture to within the range of −10° C. to +25° C. to promote the formation of a precipitate of a complex between the sulforaphane or sulforaphane analog and the cyclodextrin; and
c) collecting the precipitate formed.

It has been surprisingly found that cyclodextrin can be used to effectively isolate sulforaphane and/or a sulforaphane analog from natural sources with high levels of purity. Thus, the process of the present invention provides a simple and cost effective means of isolating naturally occurring sulforaphane or naturally occurring sulforaphane analogs.

In a second aspect, the present invention provides a method of purifying sulforaphane or a sulforaphane analog from a natural source thereof, the method comprising isolating sulforaphane and/or sulforaphane analog by the method defined herein and then releasing the sulforaphane and/or sulforaphane analog from the resultant sulforaphane-cyclodextrin or a sulforaphane analog-cyclodextrin complex.

In a third aspect, the present invention provides a method of forming a complex of sulforaphane and/or a sulforaphane analog and cyclodextrin from a natural source of sulforaphane and/or a sulforaphane analog, the method comprising:

a) mixing the natural source of sulforaphane with cyclodextrin in a suitable solvent, and with or without heat;
b) cooling or controlling the temperature of the mixture to within the range of −10° C. to +25° C. to promote the formation of a precipitate of a complex between the sulforaphane and the cyclodextrin; and
c) collecting the precipitate formed.

In a fourth aspect, the present invention relates to a complex of sulforaphane and/or sulforaphane analog with cyclodextrin formed by any one of the processes defined herein.

In a fifth aspect, the present invention relates to a complex of sulforaphane and/or sulforaphane analog with cyclodextrin obtainable by, obtained by, or directly obtained by, any one of the processes defined herein.

In a sixth aspect, the present invention relates to a complex of sulforaphane and/or sulforaphane analog with cyclodextrin prepared by any one of the methods defined herein for use in the treatment and/or prevention of microbial infections and/or cancer.

In a seventh aspect, the present invention provides a method of treating and/or preventing microbial infections and/or cancer, the method comprising administering to an individual in need of such treatment a therapeutically effective amount of a complex of sulforaphane and/or a sulforaphane analog with cyclodextrin prepared by any one of the methods defined herein.

In an eighth aspect, the present invention relates to a pharmaceutical composition comprising a complex of sulforaphane and/or sulforaphane analog with cyclodextrin prepared by any one of the methods defined herein and one or more additional pharmaceutical excipients.

DETAILED DESCRIPTION OF THE INVENTION

As indicated above, the present invention relates to a method of isolating sulforaphane and/or a sulforaphane analog from a natural source, as well as to a method of preparing a complex of sulforaphane and/or a sulforaphane analog with cyclodextrin from a natural source. The methodology comprises:

a) mixing the natural source of sulforaphane and/or sulforaphane analog with cyclodextrin in a suitable solvent, and with or without heat;

b) cooling or controlling the temperature of the mixture to within the range of −10° C. to +25° C. to promote the formation of a precipitate of a complex between the sulforaphane and/or sulforaphane analog and the cyclodextrin; and c) collecting the precipitate formed.

The methodology of the present invention effectively isolates sulforaphane and/or sulforaphane analog from the natural source in the form a high purity complex of the sulforaphane and/or sulforaphane analog with cyclodextrin.

Suitably, the purity of the sulforaphane and/or sulforaphane analog present in the complex is greater than 75%, more suitably greater than 80%, even more suitably greater than 85%, 90%, 95%, or 98%.

In some embodiments, the purity of the resulting complex can be further increased by recrystallization.

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used on another embodiment to yield a still further embodiment. Thus, it is intended that the present invention cover such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

The natural source of sulforaphane and/or sulforaphane analog utilized in the present invention may be any suitable natural source. For example, sulforaphane and/or it's analogs may be extracted from in broccoli, brussel sprouts, cabbage, cauliflower, bok choy, kale, collards, chinese broccoli, broccoli raab, kohlrabi, mustard, turnip, radish, arugula, watercress or other natural sources. Therefore, in one embodiment, the natural source is selected from one or more of these vegetable sources. Sulforaphane, or a sulforaphane analog, may be extracted directly from the source material or from extracts prepared from the natural source material.

The term "analog" or "sulforaphane analog" is used herein to refer to naturally occurring analogs of sulforaphane, such as, for example, sulforaphene, Erucin (sulforaphane with the sulphur not oxidized, i.e. methyl sulphide group) and Erysolin (sulforaphane with the sulphur over-oxidized, i.e. methyl sulfone group).

The structures of Erucin and Erysolin are shown below:

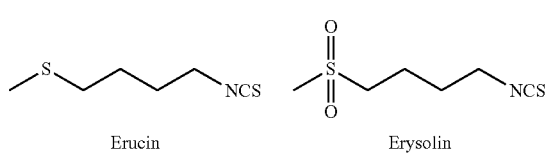

Erucin                Erysolin

Other sulforaphane analogs are known in the art and are described in, for example, U.S. Pat. Nos. 5,411,968 and 7,879,822, the entire contents of which are hereby incorporated by reference. Particular sulforaphane analogs include 6-isothiocyanato-2-hexanone; exo-2-acetyl-6-isothiocyanatonorbornane; exo-2-isothiocyanato-6-methylsulfonylnorbornane; 6-isothiocyanato-2-hexanol; 1-isothiocyanato-4-dimethylphosphonylbutane; exo-2-(1'-hydroxyethyl)-5-isothiocyanatonorbornane; exo-2-acetyl-5-isothiocyanatonorbornane; 1-isothiocyanato-5-methylsulfonylpentane; and cis- or trans-3-(methylsulfonyl)cyclohexylmethylisothiocyanate, or mixtures thereof.

Any suitable cyclodextrin may be used in the methods of the present invention. For example, the cyclodextrin for use in the methods of the present invention may be selected from one or more of W6 (alpha) cyclodextrin (a six sugar ring molecule), W7 (beta) cyclodextrin (a seven sugar ring molecule), W8 (gamma) cyclodextrin (an eight sugar ring molecule), derivatives thereof (such as hydroxyalkyl derivatives, e.g. hydroxypropyl cyclodextrin), and mixtures thereof. Other cyclodextrins known in the art are also contemplated as useful in the present composition and the invention shall not be limited to the specific cyclodextrins listed.

In an embodiment of the invention, the method of isolating sulforaphane and/or a sulforaphane analog, and the method of forming a sulforaphane-cyclodextrin complex and/or a sulforaphane analog-cyclodextrin complex includes mixing the natural source of the sulforaphane/sulforaphane analog with cyclodextrin in a suitable solvent to form a precipitate. Prior to mixing with the natural source of sulforaphane/sulforaphane analog, the cyclodextrin utilized in the present method may be dissolved in a solvent.

Any suitable solvent known in the art may be utilized in the present invention. Suitably, the solvent is an aqueous solvent comprising water and optionally one or more water-miscible solvents, such as ethanol. Suitably the solvent is water.

The dissolution of cyclodextrin in the solvent may be accomplished by any dissolution method known in the art. For example, in some embodiments, the cyclodextrin may be fully or partially dissolved in a solvent by placing cyclodextrin in the solvent and heating the mixture. In additional embodiments, sonication may be utilized to either fully or partially dissolve the cyclodextrin in the solvent. In further embodiments, multiple methods of dissolution may be utilized to reach the level of dissolution desired by the user, for example, by utilizing sonication in connection with heating the solvent.

Once the sulforaphane and/or sulforaphane analog and cyclodextrin have been added together and are ready to be mixed, any method of mixing may be utilized. For example, the components may be mixed by stirring, sonication, agitation, or other methods known in the art. In some embodiments, more than one method of mixing may be utilized together.

The duration of the mixing may vary based on the particular methods of mixing utilized. For example, if stirring or sonication is utilized, the sulforaphane and/or sulforaphane analog and cyclodextrin may be mixed for from about 2 hours to about 48 hours. In other embodiments, the sulforaphane and/or sulforaphane analog and cyclodextrin may be mixed by a stirrer or sonication for about 6 hours to about 15 hours.

As discussed above, multiple methods of mixing may be utilized for mixing the sulforaphane, or an analog thereof, and cyclodextrin. For example, in some embodiments, sonication may be utilized in connection with stirring. In such embodiments, sonication may be utilized for a duration of from about 0.01 hours to about 1.5 hours during mixing with a stirrer for from about 2 hours to about 48 hours. In other embodiments, sonication may be utilized for a duration from about 0.1 hours to about 1.5 hours during mixing with a stirrer for from about 6 hours to about 15 hours.

After the sulforaphane, or an analog thereof, and cyclodextrin have been mixed in a suitable solvent, the mixture is cooled to stabilize the formed precipitate. The particular sulforaphane or sulforaphane analog and cyclodextrin used may dictate the duration and severity of the cooling required. For example, the mixture may be cooled to a temperature within the range of about −10° C. to about 20° C., more suitably between about −10° C. to about 15° C., even more suitably between about −5° C. to about 5° C. The duration of the cooling can vary and may be, for example, from about 0.1 hours to about 5 hours. In a particular embodiment, the mixture may be cooled in a cooling device that is maintained at a temperature from about 2° C. to about 6° C., optionally for a duration of about 1 hour to about 2 hours. The precipitate may then be filtered to obtain a sulforaphane-cyclodextrin complex or sulforaphane analog-cyclodextrin complex of increased purity.

The methods utilized in the present invention result in a sulforaphane, or an analog thereof, of increased purity. In some embodiments, the present methods result in sulforaphane or sulforaphane analog within the cyclodextrin complex being greater than 75% pure sulforaphane and/or sulforaphane analog. In additional embodiments, the present methods result in sulforaphane and/or sulforaphane analogs within the sulforaphane/sulforpahane analog-cyclodextrin complex being greater than 90% pure sulforaphane and/or sulforaphane analog. In further embodiments, the present methods result in sulforaphane/sulforaphane analog within the sulforaphane/sulforaphane analog-cyclodextrin complex being greater than 99% pure sulforaphane and/or suforaphane analog.

Suitably the ratio of molar ratio of sulforaphane to cyclodextrin in the resultant complex is within the range of 0.4:1 to 1:1, suitably 0.8:1 to 1:1 and more suitably 0.9:1 to 1:1, 0.95:1 to 1:1 or 0.98:1 to 1:1.

Suitably a sufficient molar excess of the cyclodextrin is used in the methodology of the present invention.

As discussed above, in further embodiments, the resulting complex may be recrystallized to obtain a complex with an even greater purity level of the sulforaphane and/or suforaphane analog. In such embodiments, any method of recrystallization known in the art may be utilized. For example, in some embodiments, recrystallization may be accomplished by cooling the resulting mixture, by dissolving the resulting mixture in a second solvent, through a chemical reaction, by changing the pH of the mixture or by evaporating the solvent. The user's specifications may dictate the particular methods utilized.

In some embodiments, the method of recrystallization may include dissolution of the formed solid particles in a solvent. Such dissolution may be completed by any method known in the art. For example, in some embodiments, the dissolution may be completed through sonication. The sonication may be completed at an elevated temperature, i.e. from about 50° C. to about 100° C., and may be continued until no solid particles remain. Additionally, any solvent known in the art may be utilized, including those indicated above that may be useful in connection with dissolving cyclodextrin.

After dissolution has been substantially completed, the mixture may be held at room temperature to allow the solids to precipitate out of solution. Depending on the materials utilized, the time in which the mixture is held at room temperature may vary. For example, if sulforaphane is isolated, solids may completely precipitate out of solution within an hour of being held at room temperature. In other embodiments, the solution may take more than or less than an hour to sufficiently allow the solids of the complex to precipitate out of solution.

As discussed above, the solids may then be cooled to aid in stabilizing the complexed product. The particular complex used may dictate the amount of cooling necessary. For example, in some embodiments, the mixture may be cooled in a cooling device, such as for example a refrigerator, that is maintained at a temperature from about −10° C. to about 25° C., optionally for a time from about 0.1 hours to about 2 hours. In other embodiments, the mixture may be cooled in a cooling device that is maintained at a temperature from about −5° C. to about 5° C. for a time between about 0.5 hours to 24 hours. After the complex has sufficiently recrystallized, it may then be filtered to produce a sulforaphane/sulforaphane analog-cyclodextrin complex of even greater purity.

The present invention also provides a method of purifying sulforaphane and/or a sulforaphane analog from a natural source thereof, the method comprising isolating sulforaphane, or analog thereof, by the method defined herein before and then releasing the sulforaphane, or analog thereof, from the resultant sulforaphane-cyclodextrin complex or sulforaphane analog-cyclodextrin complex.

Techniques for releasing chelated compounds from cyclodextrins are well known in the art and any suitable technique may be used in the method of the present invention. In an embodiment, the method involves mixing the complex in an organic solvent or by using other methods known in the art.

In another aspect, the invention is directed to a method of providing anticancer and/or antimicrobial treatments to a subject in need of such treatment. The method includes administering to a subject in need of such treatment the sulforaphane-cyclodextrin complexes of increased purity defined herein in an effective amount.

As used herein, an "effective amount" means the dose or amount of the present invention to be administered to a subject and the frequency of administration to the subject which is readily determined by one of ordinary skill in the art, by the use of known techniques and by observing results obtained under analogous circumstances and has some therapeutic action. The dose or effective amount to be administered to a subject and the frequency of administration to the subject can be readily determined by one of ordinary skill in the art by the use of known techniques and by observing results obtained under analogous circumstances.

For ease of reference, the present invention will be described with reference to administration to human subjects. It will be understood, however, that such descriptions are not limited to administration to humans, but will also include administration to other animals, such as mammals, unless explicitly stated otherwise. For example, besides being useful for human treatment, these combinations are also useful for treatment of mammals, including horses, dogs, cats, rats, mice, sheep, pigs, etc.

A first component of the treatment method is sulforaphane, and/or an analog thereof, purified in accordance with the methods discussed above. The components that are useful in the present invention can be of any purity or grade, as long as the preparation is of a quality and stability suitable for pharmaceutical use and does not affect the resulting preparation's physiological activity or safety.

The method may further include administration of other pharmaceutically acceptable components. The term "pharmaceutically acceptable" is used adjectivally herein to mean that the modified noun is appropriate for use in a pharmaceutical product.

When the purified sulforaphane-cyclodextrin complex and/or sulforaphane analog-cyclodextrin complex created by the present methods is supplied along with a pharmaceutically acceptable carrier or pharmaceutically acceptable excipient, which terms can be used interchangeably herein, a pharmaceutical composition may be formed. The pharmaceutical compositions of the invention may be prepared by any of the well-known techniques of pharmacy, for example, by admixing the components.

A pharmaceutical composition of the present invention is directed to a composition suitable for the prevention or treatment of the disorders described herein.

Pharmaceutically acceptable carriers and excipients are chosen such that side effects from the pharmaceutical compound(s) are minimized and the performance of the compound(s) is not canceled or inhibited to such an extent that treatment is ineffective. Pharmaceutically acceptable carriers include, but are not limited to, physiological saline, Ringer's, phosphate solution or buffer, buffered saline, and other carriers known in the art. Pharmaceutical compositions may also include stabilizers, anti-oxidants, colorants, and diluents.

The carrier should be acceptable in the sense of being compatible with the other ingredients of the composition and not be deleterious to the recipient. The carrier can be a solid or a liquid, or both, and may be formulated with the compound(s) as a unit-dose composition, for example, a tablet, which can contain from about 0.01% to about 95% by weight of the active compound(s).

The pharmaceutically acceptable carrier can also be selected on the basis of the desired route of administration of the compound(s). The desired route of administration may be one or more of oral, enteral, parenteral, injectable, buccal, and topical. For example, in an embodiment, the carrier is suitable for oral administration. In some embodiments, the composition includes a carrier or additional agent that is suitable for promoting delivery of the compound(s) to the gastrointestinal or intestinal tract.

In particular, the pharmaceutical compositions of the present invention, or compositions in which they are included, can be administered orally, for example, as tablets, coated tablets, dragees, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of sweetening agents, flavoring agents, coloring agents and preserving agents in order to provide pharmaceutically acceptable and palatable preparations. Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, maize starch or alginic acid; binding agents, for example starch, gelatin, or acacia, and lubricating agents, for example magnesium stearate, stearic acid or talc. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredients are mixed with an inert solid diluent, such as for example calcium carbonate, calcium phosphate or kaolin, or as soft gelatin capsules wherein the active ingredients are present or mixed with water or an oil medium, such as for example peanut oil, liquid paraffin, any of a variety of herbal extracts, milk, or olive oil.

Aqueous suspensions can be produced that contain the active materials in admixture with excipients suitable for the manufacture of aqueous suspensions. Such excipients include suspending agents, such as for example sodium carboxymethylcellulose, methylcellulose, hydroxypropylmethyl-cellulose, sodium alginate, polyvinylpyrrolidone gum tragacanth and gum acacia; dispersing or wetting agents may be naturally-occurring phosphatides, such as for example lecithin, or condensation products of an alkylene oxide with fatty acids, such as for example polyoxyethylene stearate, or condensation products of ethylene oxide with long chain aliphatic alcohols, such as for example heptadecaethyleneoxycetanol, or condensation products of ethylene oxide with partial esters derived from fatty acids and a hexitol, such as for example polyoxyethylene sorbitol monooleate or condensation products of ethylene oxide with partial esters derived from fatty acids and hexitol anhydrides, such as for example polyoxyethylene sorbitan monooleate.

The aqueous suspensions may also contain one or more preservatives, such as for example ethyl or n-propyl p-hydroxybenzoate, one or more coloring agents, one or more flavoring agents, or one or more sweetening agents, such as sucrose, glycerol, sorbitol or saccharin.

Oily suspensions may be formulated by suspending the active ingredients in an omega-3 fatty acid, a vegetable oil, such as for example arachis oil, olive oil, sesame oil or coconut oil, or in a mineral oil such as liquid paraffin. The oily suspensions may contain a thickening agent, such as for example beeswax, hard paraffin or cetyl alcohol.

Sweetening agents, such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavoring and coloring agents, may also be present.

Syrups and elixirs containing the sulforaphane-cyclodextrin complex may be formulated with sweetening agents, such as for example glycerol, sorbitol, or sucrose. Such formulations may also contain a demulcent, a preservative, and/or flavoring and coloring agents. Liquid dosage forms for oral administration can include pharmaceutically acceptable emulsions, solutions, suspensions, syrups, and/or elixirs containing inert diluents commonly used in the art, such as water. Such compositions may also comprise adjuvants, such as wetting agents, emulsifying and/or suspending agents, and sweetening, flavoring, and/or perfuming agents.

Pharmaceutical compositions suitable for oral administration can be presented in discrete units each containing a predetermined amount of at least one therapeutic compound useful in the present invention; as a powder or granules; as a solution or a suspension in an aqueous or non-aqueous liquid; or as an oil-in-water or water-in-oil emulsion. As indicated, such compositions can be prepared by any suitable method of pharmacy, which may include the step of bringing into association the active compound(s) and the carrier (which can constitute one or more accessory ingredients). In general, the compositions are prepared by admixing the active compound with a liquid or finely divided solid carrier, or both, and then, if necessary, shaping the product.

For example, a tablet can be prepared by compressing or molding a powder or granules of the compound, optionally with one or more accessory ingredients. Compressed tablets can be prepared by compressing, in a suitable machine, the compound in a free-flowing form, such as a powder or granules optionally mixed with a binder, lubricant, inert diluent and/or surface active/dispersing agent(s). Molded tablets can be made by molding, in a suitable machine, the powdered compound moistened with an inert liquid diluent.

Oral delivery of the combinations of the present invention can include formulations, as are well known in the art, to provide prolonged or sustained delivery of the drug to the gastrointestinal and/or intestinal tract by any number of mechanisms. These include, but are not limited to, pH-sensitive release from the dosage form based on the changing pH of the small intestine, slow erosion of a tablet or capsule, retention in the stomach based on the physical properties of the formulation, bioadhesion of the dosage form to the mucosal lining of the intestinal tract, or enzymatic release of the active drug from the dosage form. For some of the therapeutic compounds useful in the methods, combinations and compositions of the present invention, the intended effect is to extend the time period over which the active drug molecule is delivered to the site of action by manipulation of the dosage form. Thus, enteric-coated and enteric-coated controlled release formulations are within the scope of the present invention. Suitable enteric coatings include cellulose acetate phthalate, polyvinylacetate phthalate, hydroxypropylmethylcellulose phthalate and anionic polymers of methacrylic acid and methacrylic acid methyl ester.

In certain embodiments, the pharmaceutical composition may include tablets that may be uncoated or they may be coated by known techniques to delay disintegration and absorption in the gastrointestinal tract and thereby provide a delayed action over a longer period. For example, a time delay material such as glyceryl monostearate or glyceryl distearate may be employed.

In additional embodiments, the compositions created by the subject method may be administered parenterally, such as for example subcutaneously, intravenously, intramuscularly, intrasternally, or by infusion techniques, in the form of sterile injectable aqueous or olagenous suspensions. The sterile injectable preparation may also be a sterile injectable solution or suspension in a non-toxic parenterally acceptable diluent or solvent, such as for example a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed, including synthetic mono- or diglycerides. In addition, n-3 polyunsaturated fatty acids may find use in the preparation of injectables.

Pharmaceutical compositions suitable for parenteral administration can comprise sterile aqueous preparations of a compound of the present invention. These preparations may be administered intravenously, although administration can also be effected by means of subcutaneous, intramuscular, or intradermal injection or by infusion. Such preparations may be prepared by admixing the compound with water and rendering the resulting solution sterile and isotonic with the blood. Injectable compositions according to the invention will generally contain from 0.01 to 10% w/w of a compound disclosed herein.

The active ingredients may also be administered by injection as a composition wherein, for example, saline, dextrose, or water may be used as a suitable carrier. A suitable daily dose of each active therapeutic compound is one that achieves relatively the same blood serum level as produced by oral administration as described above.

Also encompassed by the present invention is buccal or "sub-lingual" administration, which includes lozenges or a chewable gum comprising the compounds set forth herein. The compounds can be deposited in a flavored base and acacia or tragacanth or the compounds may be deposited in pastilles comprising the compounds in an inert base such as gelatin and glycerin or sucrose and acacia.

The pharmaceutical compositions of the present invention are also suitable for topical application to the skin and may take the form of ointments, creams, lotions, pastes, gels, sprays, powders, jellies, collyriums, solutions, suspensions, aerosols, or oils. Carriers may be used and include petroleum jelly (e.g., Vaseline®), lanolin, polyethylene glycols, alcohols, and combinations of two or more thereof. The active compound or compounds are generally present at a concentration of from 0.01 to 50% w/w of the composition, such as for example from about 0.01 to about 2%.

The present invention may also include safe and effective amounts of isotonicity agents, including, salts, such as sodium chloride, and/or non-electrolyte isotonicity agents such as sorbitol and mannitol.

The solubility of the components of the present compositions may be enhanced by a surfactant or other appropriate co-solvent in the composition. Such co-solvents include polysorbate 20, 60, and 80, polyoxyethylene/polyoxypropylene surfactants (e.g., Pluronic F-68, F-84 and P-103, available from BASF®), cyclodextrin, or other agents known to those skilled in the art. Such co-solvents may be employed at levels of from about 0.01% to about 2% by weight.

Pharmaceutically acceptable excipients and carriers encompass all the foregoing and the like. Effective formulations and administration procedures are well known in the art and are described in standard textbooks. See e.g. Gennaro, A. R., *Remington: The Science and Practice of Pharmacy*, 20$^{th}$ Edition, (Lippincott, Williams and Wilkins), 2000; Hoover, John E., *Remington's Pharmaceutical Sciences*, Mack Publishing Co., Easton, Pa., 1975; Liberman, et al., Eds., *Pharmaceutical Dosage Forms*, Marcel Decker, New York, N.Y., 1980; and Kibbe, et al., Eds., *Handbook of Pharmaceutical Excipients* (3$^{rd}$ Ed.), American Pharmaceutical Association, Washington, 1999.

In the present method, a subject in need of treatment and/or prevention of the disorders described herein and/or related conditions may be treated with an amount of the presently inventive purified sulforaphane, or analog thereof, wherein the amount of the individual components provides a dosage or amount that is sufficient to constitute a treatment or prevention effective amount.

The effective amount of purified sulforaphane-cyclodextrin complex or sulforaphane analog-cyclodextrin complex, of course, depend on a number of factors, such as the specific compound chosen, the use for which it is intended, the mode of administration, the host to be treated, and the clinical condition of the recipient.

A carcinogenic, tumorigenic, or anti-bacterial symptom is considered ameliorated or improved if any benefit is achieved, no matter how slight.

Dosages for the present compositions and methods provided herein may be determined and adjusted based on the efficacy demonstrated in providing a chemoprotective or chemopreventative result. In addition, one of ordinary skill in the art will know how to measure and quantify the presence or absence of carcinogenesis or tumorigenesis symptoms.

Dosages for the present compositions are those that are effective to provide a chemoprotective, chemopreventative, and/or anti-bacterial effect.

Those skilled in the art will appreciate that dosages may also be determined with guidance from Goodman & Gilman's *The Pharmacological Basis of Therapeutics*, Ninth Edition (1996), Appendix II, pp. 1707-1711.

The following examples describe various embodiments of the present invention. Other embodiments within the scope of the claims herein will be apparent to one skilled in the art from consideration of the specification or practice of the invention as disclosed herein. It is intended that the specification, together with the examples, be considered to be exemplary only, with the scope and spirit of the invention being indicated by the claims which follow the examples.

EXAMPLES

General Materials and Methods $^1$H and $^{13}$C NMR spectra were recorded on a Oxford 400 MHz spectrometer using TMS as the internal standard and the chemical shifts are reported in ppm.

HPLC was performed on a HP 1050 Module, Column: Phenomenex Gemini C18, 5μ, 110 Å, 250×4.6 mm. Total run time: 40 min. MeCN in H2O+0.1% TFA. Flow: 1.5 mL/min. Detector: 244 nm (VWD).

Example 1

This example is directed to an embodiment of the present invention demonstrating an improved method for purifying sulforaphane.

A sulforaphane sample (mfg: Beijing Hunda Qunxing Science and Technology Co.; Lot #20091101) (8.23 g, 11.3 mmol of sulforaphane @ 24.3% purity) was loaded into a 250 mL round bottom flask equipped with a magnetic stirrer and 43.9 mL of a 0.257M cyclodextrin solution (mfg: Wacker; Lot #60F212; 11.3 mmol of cyclodextrin) was added. The cyclodextrin solution was prepared by heating 288.9 g of cyclodextrin at 70° C. with sonication in 1 L of water to give a total volume of 1155 mL after complete dissolution of the cyclodextrin.

The mixture was stirred at room temperature for one hour, sonicated for 10 minutes, and then stirred for another two hours. A small amount of precipitate formed. Stirring was continued overnight, which resulted in an increased amount of precipitate. The mixture was cooled at 4° C. in a refrigerator for one hour and filtered to give 3.95 g (30.5% yield, 97% purity by HPLC) of an off-white solid. The reading obtained by the HPLC was consistent with a 0.95:1 ratio of sulforaphane to cyclodextrin.

$^1$HNMR (D$_2$O, 400 MHz); δ 1.99 (br, 4H), 2.75 (s, 3H), 3.01 (br, 2H), 3.60 (m, 12H), 3.75 (br, 2H), 3.90 (m, 24H), 5.12 (d, 6H).

$^{13}$CNMR (D$_2$O, 100 MHz); δ 130.07, 101.81, 81.39, 74.04, 71.96, 71.85, 60.32, 52.02, 44.99, 37.08, 29.40, 20.11.

Both the $^{13}$C NMR analysis and $^1$H NMR analysis were consistent with a 1:0.95 ratio of sulforaphane to cyclodextrin.

Example 2

This example is directed to an additional embodiment of the present invention demonstrating an improved method for purifying sulforaphane.

A sulforaphane sample (mfg: Beijing Hunda Qunxing Science and Technology Co.; Lot #20091101) (3.2 g, 11.3 mmol of sulforaphane @ 62.9% purity) was loaded into a 250 mL round bottom flask equipped with a magnetic stirrer and 43.9 mL of 0.257 M cyclodextrin in water was added to the flask. The cyclodextrin solution was prepared by heating 288.9 g of cyclodextrin at 70° C. with sonication in 1 L of water to give a total volume of 1155 mL after complete dissolution of the cyclodextrin.

The solution was stirred at room temperature for 1 hour, sonicated for 10 minutes, and then stirred again for 2 hours. After precipitate formed, the mixture was cooled at 4° C. in a refrigerator overnight. After more solid precipitated, the mixture was filtered to give 11.9 g (92% yield, 96% purity by HPLC) of a pale yellow solid. The HPLC analysis indicated a 0.93:1 ratio of sulforaphane to cyclodextrin.

$^1$HNMR (D$_2$O, 400 MHz); δ 1.99 (m, 4H), 2.75 (s, 3H), 3.01 (t, 2H), 3.60 (m, 12H), 3.76 (br, 2H), 3.91 (m, 24H), 5.05 (d, 6H)

$^{13}$CNMR (D$_2$O, 100 MHz); δ 129.94, 101.79, 81.40, 73.99, 71.96, 71.84, 60.34, 52.02, 44.94, 37.03, 29.29, 20.08.

Both the $^{13}$C NMR analysis and $^1$H NMR analysis were consistent with a 1:1.04 ratio of sulforaphane to cyclodextrin.

Example 3

The sulforaphane-cyclodextrin complex (2.2 g, 1.9 mmol) obtained in Example 2 was loaded into a 20 mL scintillation vial and 6 mL of water was added. The mixture was sonicated at about 70° C. until dissolution of the solid particles was complete. The vial was then removed from the sonication bath and kept at room temperature for one hour. Solids started precipitating out of solution. The vial was moved into a refrigerator at 4° C. for 30 minutes and filtered to give an off-white solid that was dried in a vacuum oven at 30° C. overnight. Recrystallization yielded 1.5 g of an off-white solid (68% yield, 98% purity by HPLC).

$^1$HNMR (D$_2$O, 400 MHz); δ 2.01 (br, 4H), 2.78 (s, 3H), 3.01 (br, 2H), 3.65 (m, 12H), 3.75 (br, 2H), 3.91 (m, 24H), 5.15 (d, 6H)

$^{13}$CNMR (D$_2$O, 100 MHz); δ 129.98, 101.79, 81.39, 74.01, 71.95, 71.83, 60.31, 52.01, 44.95, 37.04, 29.33, 20.08

Both a $^{13}$C NMR and $^1$H NMR analysis (Figures 8 and 9) were consistent with a 1:1.02 ratio of sulforaphane to cyclodextrin.

These examples demonstrate the efficacy of the present methods for providing sulforaphane of increased purity.

All references cited in this specification, including without limitation, all papers, publications, patents, patent applications, presentations, texts, reports, manuscripts, brochures, books, internet postings, journal articles, periodicals, and the like, are hereby incorporated by reference into this specification in their entireties.

The discussion of the references herein is intended merely to summarize the assertions made by their authors and no admission is made that any reference constitutes prior art. Applicants reserve the right to challenge the accuracy and pertinency of the cited references.

Although embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged both in whole or in part.

What is claimed is:

1. A method of isolating sulforaphane and/or a sulforaphane analog from a natural source thereof, the method comprising:
   a) mixing the natural source of sulforaphane and/or sulforaphane analog, or an extract prepared from the natural source, wherein the purity of the sulforaphane and/or the sulforaphane analog in the extract is less than 75%, with cyclodextrin in a suitable solvent and with or without heat;
   b) cooling the mixture to a temperature within the range of −10° C. to +25° C. to promote the formation of a precipitate of a complex between the sulforaphane or sulforaphane analog and the cyclodextrin; and
   c) collecting the precipitate formed.

2. A method according to claim 1, wherein the cyclodextrin is selected from the group consisting of W6 (alpha) cyclodextrin, W7 (beta) cyclodextrin, W8 (gamma) cyclodextrin, derivatives thereof, and mixtures thereof.

3. A method according to claim 1, wherein the cyclodextrin is W6 (alpha) cyclodextrin.

4. A method according to claim 1, wherein the analog of sulforaphane is selected from the group consisting of sulforaphene, Erucin, Erysolin, and mixtures thereof.

5. A method according to claim 1, wherein the method further comprises:
   dissolving the cyclodextrin in a solvent prior to mixing with the sulforaphane or an analog thereof.

6. A method according to claim 5, wherein the solvent is water.

7. A method according to claim 1, wherein the mixture is cooled to a temperature of between about −10° C. to about 15° C.

8. A method according to claim 1, wherein the mixture is cooled to a temperature of between about −5° C. to about 5° C.

9. A method according to claim 1, wherein the method further comprises recrystallizing the precipitate and filtering the resulting solid from the recrystallization.

10. A method according to claim 9, wherein the recrystallization is accomplished by dissolving the precipitate in a solvent and cooling the mixture of the precipitate and the solvent to below room temperature and filtering the resulting solid.

11. A method according to claim 1, wherein the purity of the sulforaphane and/or a sulforaphane analog in the extract prepared from the natural source is less than about 63%.

12. A method according to claim 1, wherein the purity of the sulforaphane and/or a sulforaphane analog in the extract prepared from the natural source is less than about 24%.

* * * * *